United States Patent [19]

Lindegren

[11] Patent Number: 6,102,753
[45] Date of Patent: Aug. 15, 2000

[54] ELECTRICAL FEMALE CONNECTOR, ESPECIALLY FOR AN IMPLANTABLE HEART STIMULATOR

[75] Inventor: Ulf Lindegren, Enskede, Sweden

[73] Assignee: Pacesetter AB, Järfälla, Sweden

[21] Appl. No.: 09/194,238

[22] PCT Filed: May 12, 1997

[86] PCT No.: PCT/SE97/00771

§ 371 Date: Jun. 1, 1999

§ 102(e) Date: Jun. 1, 1999

[87] PCT Pub. No.: WO97/44091

PCT Pub. Date: Nov. 27, 1997

[30] Foreign Application Priority Data

May 23, 1996 [SE] Sweden ................................. 9601972

[51] Int. Cl.[7] .................................................. H01R 11/22
[52] U.S. Cl. ............................ 439/848; 439/909; 607/37
[58] Field of Search ..................... 439/848, 161, 439/197, 835, 851, 909; 607/37

[56] References Cited

U.S. PATENT DOCUMENTS

| 4,278,093 | 7/1981 | Lafortune et al. ...................... 607/307 |
| 4,848,346 | 7/1989 | Crawford .................................. 607/37 |
| 4,934,366 | 6/1990 | Truex et al. .............................. 607/37 |
| 5,012,807 | 5/1991 | Stutz, Jr. ................................... 607/37 |
| 5,070,605 | 12/1991 | Daglow et al. ........................... 29/842 |
| 5,507,662 | 4/1996 | Nyman ..................................... 439/348 |
| 5,735,716 | 4/1998 | Bilezikjian .............................. 439/843 |
| 5,766,042 | 6/1998 | Ries et al. ................................ 439/668 |
| 6,044,302 | 3/2000 | Persuitti et al. .......................... 607/37 |

FOREIGN PATENT DOCUMENTS

| 0 339 877 | 11/1989 | European Pat. Off. . |
| 0 590 756 | 4/1994 | European Pat. Off. . |
| WO 93/05844 | 4/1993 | WIPO . |

Primary Examiner—Khiem Nguyen
Assistant Examiner—Son V. Nguyen
Attorney, Agent, or Firm—Hill & Simpson

[57] ABSTRACT

An electrical female connector for affixing a contact pin of an electrode cable in a connector part of a heart stimulator has a sleeve which is elastic and which has a curved shape in a relaxed condition. The sleeve is straightened to a substantially straight configuration when the contact pin is inserted into the sleeve, and thereupon rebounds back to a partially curved configuration so as to clamp the contact pin inside the sleeve.

10 Claims, 1 Drawing Sheet

6,102,753

ELECTRICAL FEMALE CONNECTOR, ESPECIALLY FOR AN IMPLANTABLE HEART STIMULATOR

FIELD OF THE INVENTION

The present invention relates to an electrical female connector, especially for establishing contact with a contact pin on the proximal end of an electrode cable which is connectable to an implantable heart stimulator, such as a pacemaker or defibrillator, whereby the female connector has an electrically conductive sleeve; arranged in a connector part of the heart stimulator.

DECSRIPTION OF THE PRIOR ART

A commonly found connector for this purpose in the general form includes a metal sleeve in which the electrode cable's contact pin is inserted and affixed with a locking screw accessible from the outside of the connector part. The locking screw achieves contact between the sleeve and the pin and simultaneous axial locking of the electrode cable, thereby preventing detachment of the electrode cable from the connector part. This fixation method requires the use of screwdrivers, tiny mechanical screws and special seals for same.

Connectors for this purpose have also been proposed which are capable of achieving automatic contact between the contact pin and the female connector when the electrode contact pin is inserted into the connector. For example, U.S. Pat. No. 4,934,366 and U.S. Pat. No. 5,012,807 describe such female connectors which are formed from a torus-shaped spring which radially presses against a corresponding contact surface on the pin when the pin is inserted, thereby achieving mechanical contact on all sides between the male contact pin on the electrode and the female connector built into the heart stimulator's connector part. Contact points are sealed with separate seals devised on the exterior of the contact pin end of the electrode cable and/or on the inside the connector. European application 0339877 shows a connector for a pacemaker, this connector having electrically conductive elastomer rings which permit both a positive mechanical connection and, accordingly, electrical contact between contact surfaces and simultaneous sealing to keep fluid from reaching the contact pin. These contact rings do not have any well-defined contact and sealing surfaces, so the electrically conductive elastic rings must be supplemented with separate sealing rings in order to achieve efficient sealing of contact surfaces.

U.S. Pat. No. 4,848,346 describes a connector for a pacemaker in which the contactarrangement is formed by a spring ring which can be expanded by depressing a shaft section, projecting from the connector part, of the spring, in order to permit the insertion of an electrode cable's contact pin. However, such a projecting operating element can cause inadvertent detachment of the electrode cable.

Another way of affixing an electrode cable pin in the connector part of a heart stimulator is described in European application 0590756. Here, the afixing device is formed by a spring plate, molded into the connector, with opposing, resilient gripping tongues designed to grip the cable's contact pin while simultaneously preventing any detachment of the electrode cable from the connector arrangement, the retention force of the clamp thereby increasing when an detachment force is exerted on the electrode cable. The grip of the gripping tongues on the cable end's contact pin could cease if pressure were exerted on the spring plate's opposing, projecting lateral tips.

SUMMARY OF THE INVENTION

An object of the present invention is to provide a female connector of the kind cited initially with which a contact pin can be quickly affixed to the connector part with a simple manual operation.

For this purpose, the female connector according to the invention is characterized by an elastic sleeve which has a curved shape in the relaxed state, the sleeve being arranged so it can be made to assume an essentially straight conformation to permit insertion of the contact pin into the sleeve. When the contact pin has been inserted into the sleeve means, after the sleeve has been straightened into an essentially straight conformation, which can be accomplished with an external aid in the form of a detachable pressure element or with the aid of the contact pin itself, the elastic sleeve strives to resume its original curved shape. This then clamps the contact pin inside the sleeve as a result of the friction forces between them. In straightening out the sleeve, the pressure element is arranged to be inserted into a hole, essentially perpendicular to the longitudinal axis of the sleeve, in the connector part.

The pressure element suitably has a shaft part, insertable in the hole, and an external push-button.

The sleeve, which is preferably made of a superelastic alloy of nickel and titanium, such as nitinol, capable of elastically stretching up to about 10%, is suitably embedded in some elastic substance, such as silicone, so the contact sleeve can be elastically suspended in and sealed against the entry of body fluid.

In order to achieve positive locking of the contact pin in the sleeve, an inward-projecting locking pin can be arranged inside the sleeve so as to engage a circular slot in the contact pin.

DESCRIPTION OF THE PREFERRED EMBODIMENTS

Figure 1:
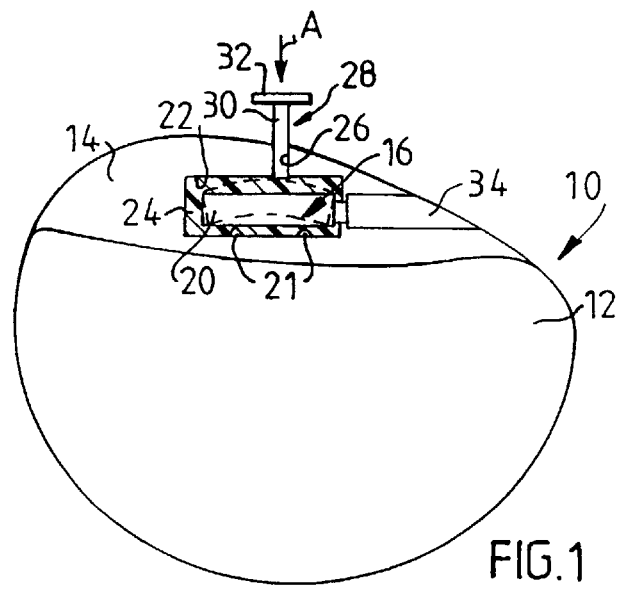
FIG. 1 is a schematic side view of a pacemaker with a unipolar female connector according to the invention, shown with solid lines in a pre-tensioned, straightened position and with dashed lines in a relaxed, unloaded, curved condition.

In FIG. 1 a pacemaker which has an enclosure 12 containing an electronics unit and battery (not shown), plus a molded-on superstructure or connector part 14 to hold a female connector 16 for connecting the proximal end contact pin 18 (FIGS. 3 and 4) of a conductive electrode cable (not shown) leading to the heart.

Figure 2:
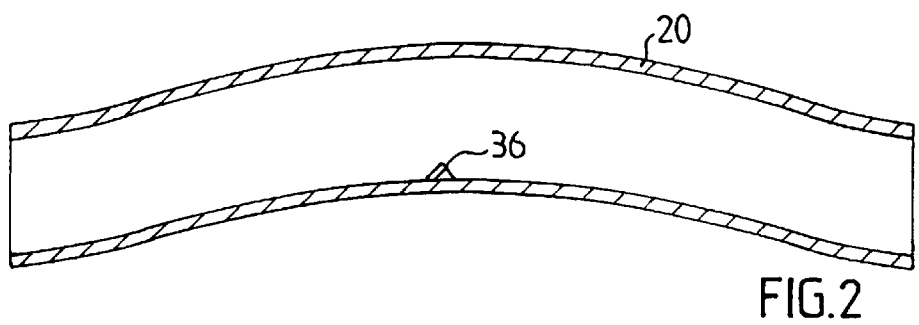
FIG. 2 is an enlargement (not to scale) of the sleeve-shaped connector of FIG. 1 in the relaxed, curved condition.

The female connector 16 according to the invention has a sleeve 20 made of an elastic alloy, preferably a superelastic alloy of e.g. nickel and titanium, such as nitinol, which can be elastically stretched up to about 10%, as opposed to about 0.2% for other alloys. As is best shown in FIG. 2, the sleeve 20 has a precurved shape in the relaxed, unloaded state and is inside a compartment 22 in the connector part 14, surrounded by a sealing substance 24 made of e.g. silicone (FIG. 1). In one practical embodiment, the contact pin 18, which is tubular to permit insertion of a stylet, can be about 5.6 mm long and about 1.5 mm in diameter. The sleeve 20 can have an internal diameter of about 2.0 mm and a wall thickness of about 0.4 mm.

Figure 3:
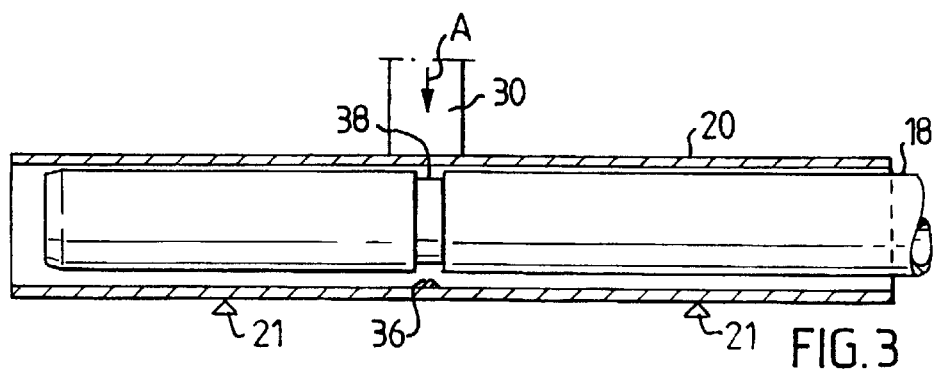
FIG. 3 shows the sleeve of FIG. 2 straightened with an external pressure element to permit insertion of a proximal electrode cable pin into the sleeve.

The connector part 14 has a hole 26 which opens into the compartment 22 and is essentially perpendicular to the sleeve 20 opposite the latter's midsection. The hole 26 is a guide hole for a pressure element 28, insertable therein, which has a shaft section 30, moveable in the hole 26, and a push-button 32. The task of the pressure element 28, when pressure is manually applied to it in the direction of the arrow A in FIGS. 1 and 3, is to force the curved sleeve 20 to assume an essentially straight, pre-tensioned conformation, enabling the contact pin 18 on the proximal end of the electrode cable to be inserted into the contact sleeve 20 through an entry hole 34 in the connector section 14. The sleeve 20 is guided on its longitudinal sides by the nearby walls of the compartment 22 to keep the sleeve 20 from veering during its straightening and can rest on the abutment 21 at the bottom of the compartment 22.

Figure 4:
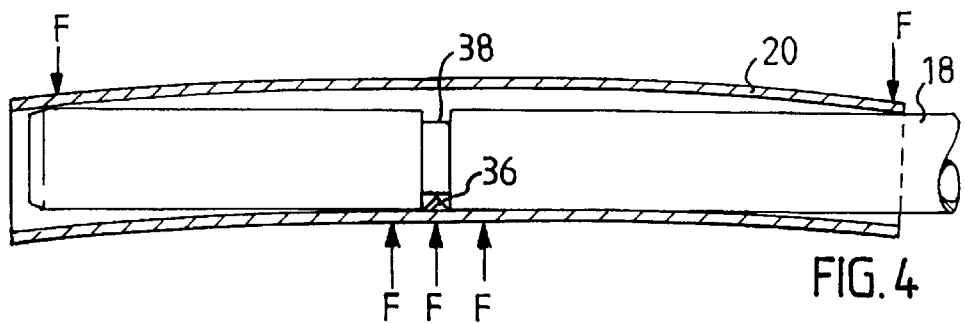
FIG. 4 shows an active affixing arrangement for keeping the contact pin affixed inside the sleeve.

FIG. 3 shows in an enlarged view, not to scale, the phase in which the contact pin 18 has just been inserted into the sleeve 20. The inside of the sleeve 20 can have a projecting locking pin intended to engage a corresponding groove or track 38 in the contact pin 18 when perpendicular pressure on the sleeve 20 has terminated, the sleeve thereupon striving to resume its original curved shape in order to clamp the pin 18 in the sleeve 20 and create good electrical contact between them. The locking pin 36 can project about 0.3 mm from the interior wall of the sleeve 20, and the groove 38 can be about 0.2 mm deep. FIG. 4 depicts the fixation position between the sleeve 20 and the pin 18 showing how the sleeve 20 has partially rebounded back to its curved conformation and is clamping the contact pin 18 at the points designated with the arrows F. Here, the locking pin 36 has engaged the groove 38 in order to on one hand achieve blocking which prevents axial detachment of the contact pin from the sleeve 20, and on the other hand improve contact between the sleeve and the pin. An appropriate stop (not shown) can be arranged in the sleeve 20 and/or the contact pin 18 to limit insertion of the pin to a position at which the locking pin 36 is opposite the groove 38.

According to an alternative embodiment of the invention, the pressure element 28 can be excluded and the sleeve 20 can be devised to be straightened by the contact pin 18 when the latter is inserted into the sleeve 20. The pin 18 should then be kept in an axially fixed position in relation to the compartment 22.

Although the above-described embodiment of the female connector according to the invention is a unipolar design, the principle can also be applied to bipolar or multipolar contact pins through the provision of a number of elastic, precurved contact sleeves.

Although modifications and changes may be suggested by those of ordinary skill in the art, it is the intention of the inventor to embody within the patent warranted hereon all changes and modifications as reasonably and properly come within the scope of this contribution to the art.

What is claimed is:

1. An electrical female connector for establishing contact with a contact pin at a proximal end of an electrode cable connectable to an implantable heart stimulator, said female connector comprising an electrically conductive sleeve contained in a connector part, said sleeve being elastic and having a curved shape in a relaxed state, said sleeve being straightenable into a substantially straight configuration for allowing insertion of said contact pin into said sleeve.

2. A female connector as claimed in claim 1 wherein said sleeve has a longitudinal axis and wherein said connector part has a hole therein disposed substantially perpendicularly to said longitudinal axis of said sleeve, and said female connector further comprising a pressure element insertable into said hole for exerting perpendicular pressure on said sleeve.

3. A female connector as claimed in claim 2 wherein said pressure element comprises a shaft part insertable in said hole, and an externally accessible push button connected to said shaft part.

4. A female connector as claimed in claim 1 wherein said sleeve is straightened by said contact pin only when said contact pin is inserted into said sleeve.

5. A female connector as claimed in claim 1 wherein said connector part comprises an elastic material in which said sleeve is embedded.

6. A female connector as claimed in claim 5 wherein said elastic material comprises silicone.

7. A female connector as claimed in claim 1 wherein said sleeve is comprised of a super-elastic alloy.

8. A female connector as claimed in claim 7 wherein said super-elastic alloy consists of nickel and titanium.

9. A female connector as claimed in claim 7 wherein said super-elastic alloy comprises nitinol.

10. A female connector as claimed in claim 1 wherein said sleeve has an interior with an inwardly projecting locking pin, and wherein said contact pin has a peripheral groove adapted to engage said locking pin.

\* \* \* \* \*